(12) United States Patent
Beilfuss et al.

(10) Patent No.: US 8,841,349 B2
(45) Date of Patent: Sep. 23, 2014

(54) STABILIZE COMPOSITIONS BASED ON MONOALKYL GLYCEROL ETHERS AND AROMATIC ALCOHOLS

(75) Inventors: Wolfgang Beilfuss, Hamburg (DE); Ralf Gradtke, Tornesch (DE); Petra Kolditz, Hamburg (DE); Klaus Weber, Hamburg (DE)

(73) Assignee: Air Liquide Sante (International), Paris (FR)

( * ) Notice: Subject to any disclaimer, the term of this patent is extended or adjusted under 35 U.S.C. 154(b) by 1668 days.

(21) Appl. No.: 11/003,280

(22) Filed: Dec. 3, 2004

(65) Prior Publication Data

US 2005/0154067 A1 Jul. 14, 2005

(30) Foreign Application Priority Data

Dec. 5, 2003 (DE) ................................ 103 56 846

(51) Int. Cl.
*A01N 31/14* (2006.01)
*A61K 31/075* (2006.01)
*A01N 31/02* (2006.01)

(52) U.S. Cl.
CPC ..................................... *A01N 31/02* (2013.01)
USPC .......................................................... 514/715

(58) Field of Classification Search
USPC .......................................................... 514/715
See application file for complete search history.

(56) References Cited

U.S. PATENT DOCUMENTS

| | | | | |
|---|---|---|---|---|
| 5,516,510 A | * | 5/1996 | Beilfuss et al. | 424/65 |
| 5,539,001 A | | 7/1996 | Waldmann-Laue et al. | |
| 5,670,160 A | | 9/1997 | Eggensperger et al. | |
| 2004/0059006 A1 | * | 3/2004 | Beilfuss et al. | 514/718 |
| 2010/0331426 A1 | * | 12/2010 | Beilfuss et al. | 514/718 |

FOREIGN PATENT DOCUMENTS

EP 1 157 687 11/2001
WO WO 0193825 A1 * 12/2001

OTHER PUBLICATIONS

European Search Report for EP 04 10 6182, 2005.

* cited by examiner

*Primary Examiner* — Samira Jean-Louis
(74) *Attorney, Agent, or Firm* — Young & Thompson

(57) ABSTRACT

A stabilizer composition having (a) one or more 1- or 2-($C_1$- to $C_{24}$-alkyl) glycerol ethers (glycerol monoalkyl ethers) and (b) a mixture of at least two different aromatic alcohols (b1, b2) chosen from the groups of i) aryloxyalkanols, ii) arylalkanols and iii) oligoalkanol aryl ethers, where the two different aromatic alcohols belong to different groups i), ii) and iii).

5 Claims, No Drawings

STABILIZE COMPOSITIONS BASED ON MONOALKYL GLYCEROL ETHERS AND AROMATIC ALCOHOLS

This application claims the benefit of priority under 35 U.S.C. §119 (a) and (b) 1 to German Application No. DE 103 56 846.8, filed Dec. 5, 2003, the entire contents of which are incorporated herein by reference.

BACKGROUND

The present invention relates to stabilizer compositions based on monoalkyl glycerol ethers and aromatic alcohols and use thereof.

Stabilizer compositions are used in many aqueous systems in order to control microbial growth. An important field of use is cosmetic formulations, such as creams, lotions, sunscreen products, shampoos, shower gels and bathing additives. Stabilizer compositions can also be used in cleaning, care and hygiene products for the home (e.g. hand washing preparations), and in many technical sectors, e.g. in cutting fluids, diesel fuels, paints and coatings.

There continues to be a great need for improved compositions which have a broad spectrum of activity towards bacteria, yeasts, moulds and viruses, develop their biocidal effectiveness (killing of microorganisms) under conditions met in practice even at low use concentrations and—particularly in the case of cosmetic and pharmaceutical preparations—are highly physiologically compatible.

It is known that glycerol monoalkyl ethers have or support antimicrobial effects. Of particular suitability is 1-(2-ethylhexyl) glycerol ether, which is available under the trade name Sensiva® SC 50 (Schülke & Mayr GmbH, Germany). However, glycerol monoalkyl ethers on their own do not have a broad spectrum of activity towards gram-positive and gram-negative bacteria, fungi, yeasts and viruses, as is necessary in specific dermatological preparations, such as, for example, skin antiseptics.

DE 42 40 674 C2 relates to deodorizing glycerol monoalkyl ethers, the 2-ethylhexyl group being specified as the alkyl group. The monoalkyl glycerol ethers can be used in combination with one or more other deodorizing substances, specifically suitable deodorizing substances being, for example, phenoxyethanol and phenethyl alcohol.

DE-A-40 26 756 discloses a preservative which comprises a mixture of a) organic acid, b) aromatic alcohol and c) guanidine derivative, where the presence of d) substituted glycerol ether is optionally possible. Example 11 discloses a mixture of, inter alia, phenoxyethanol, phenoxybutanol and 3-octyloxypropane-1-2-diol.

DE-A-41 24 664 discloses mixtures of (A) arylalkanol with diol as preservative, where glycerol monoalkyl ethers are intended as diols. DE-A-100 28 638 relates to storage-stable compositions of glycerol monoalkyl ethers which, as well as comprising glycerol monoalkyl ether and antioxidant, can also comprise additives such as benzyl alcohol, phenyl alkanol.

DE-A-100 25 123 relates to cosmetic deodorants which comprise an active ingredient combination which comprises (I) one or more substances chosen from the group of mono- and oligoglycerol monocarboxylic acid monoesters, (II) one or more aryl compounds and (III) one or more glycerol ethers. Preferred aryl compounds are chosen from the group consisting of phenoxyethanol, anis alcohol, 2-methyl-5-phenylpentan-1-ol and 2-methyl-4-phenylbutan-2-ol. DE-A-100 25 124 relates to preparations with a content of a combination of (A) an active ingredient or two or more active ingredients chosen from the group of glycerol monoalkyl ethers and (B) an active ingredient or two or more active ingredients chosen from the group of aryl-substituted alcohols.

The application DE 102 24 979, filed by the applicant and published subsequently, relates to synergistic preparations based on mixtures of glycerol ethers with aromatic alcohol for controlling mycobacteria. A disinfectant is described which comprises (a) alkyl glycerol ether and (b) one or more aromatic alcohols.

However, a disadvantage of combinations of monoalkyl glycerol ethers with aromatic alcohol has now been found to be that the combinations do not always have reliable protection when incorporated into water-based products. This is attributable, inter alia, to the fact that, on the one hand, both monoalkyl glycerol ethers and aromatic alcohols have limited solubility in water and, on the other hand, certain maximum concentrations must not be exceeded.

For example, the Cosmetics Directive (dated Jun. 14, 2000, BGB1 I, p. 846, Annex 6, Part A) stipulates certain maximum concentrations (e.g. benzyl alcohol maximum 1.0% by weight, phenoxyethanol maximum 1.0% by weight, 1-phenoxy-2-propanol maximum 1.0% by weight). Furthermore, due to the limited solubility in water of glycerol monoalkyl ethers and aromatic alcohols, certain mixing ratios of the combination with water are excluded, for which reason preferred concentrates of the prior art are anhydrous.

Thus, in numerous cosmetic bases, combinations of monoalkyl glycerol ethers with aromatic alcohol do not achieve adequate protection against microbial growth if the physically possible or permissible amount of the constituents is used: the limited solubility is an obstacle to increasing the use concentration, and in addition permissible maximum concentrations would then be exceeded. Stabilizer compositions should, however, be able to be used as diversely as possible, thus both be able to be incorporated into aqueous solutions to form clear mixtures, and also to be reliably effective in possibly ointment-like cosmetic products while observing the permissible maximum concentration.

Although it would be possible to include conventional active ingredients in the formulation in order to further increase the effectiveness of combinations of glycerol monoalkyl ether and aromatic alcohol, numerous conventional active ingredient have disadvantages. Thus, for example, an oestrogenic effect or an endocrinal potential of phenols and parabens has been reported. Organohalogen compounds, such as iodopropynyl butylcarbamate, dibromodicyanobutane and 2-bromo-2-nitro-1,3-propanediol are not adequately environmentally compatible. Formaldehyde and formaldehyde donor compounds are suspected of being carcinogenic, and carboxylic acids, such as sorbic acid, are only effective at pH values less than 6 and can lead to discolorations. In addition, the use of such conventional active ingredients may lead to incompatibilities in the stabilized product or, in the case of application of the product, for example a cosmetic and/or pharmaceutical product, to allergic reactions.

SUMMARY

The object of the invention was thus to provide a stabilizer composition for cosmetic, dermatological, pharmaceutical, technical and/or household products which, in particular,
   protects the stabilized products effectively against attack by microorganisms, or assists this protection,
   does not have incompatibilities with the other constituents of the stabilized product, does not have an irritative or drying effect upon contact of the product with the human skin (i.e. does not automatically have a high content of lower alcohols, such as ethanol or isopropanol) and can be mixed with water in broad mixing ratios.

The achievement of these objects consists in a stabilizer composition which comprises (a) one or more 1- or 2-($C_1$- to $C_{24}$-alkyl) glycerol ethers (glycerol monoalkyl ethers) and (b) a mixture of at least two different aromatic alcohols (b1, b2) chosen from the groups of i) aryloxyalkanols, ii) arylalkanols and iii) oligoalkanol aryl ethers, where the two different aromatic alcohols belong to different groups i), ii) and iii).

DESCRIPTION OF PREFERRED EMBODIMENTS

It is prescribed according to the invention that in the mixture of at least two different aromatic alcohols the two different aromatic alcohols belong to different groups. This means that in the presence of an aryloxyalkanol, at least one arylalkanol and/or oligoalkanol aryl ether must be present, that in the presence of an arylalkanol at least one aryloxyalkanol and/or oligoalkanol aryl ether must be present, and in the presence of an oligoalkanol aryl ether at least one aryloxyalkanol and/or arylalkanol must be present. In this connection, preference is given to an embodiment in which the two different aromatic alcohols belong to the groups (i) and (ii), i.e. the mixture comprises an aryloxyalkanol and a arylalkanol, where the further presence of aryloxyalkanols, arylalkanols and/or oligoalkanol aryl ethers in the mixture is possible in this embodiment.

The alkyl group of the glycerol monoalkyl ether may be a branched or unbranched $C_3$-$C_{18}$-alkyl group, where the alkyl group may be substituted by one or more hydroxyl and/or $C_1$- to $C_4$-alkoxy group(s) and/or the alkyl chain may be interrupted by up to 4 oxygen atoms.

In this connection, preference is given to alkyl groups R which are a branched or unbranched $C_3$- to $C_{18}$-hydrocarbon group, preferably a branched or unbranched $C_6$- to $C_{12}$-hydrocarbon group, more preferably a branched or unbranched octyl group and in particular a 2-ethylhexyl group.

Examples of glycerol monoalkyl ethers which can be used according to the invention are glycerol monoalkyl ethers substituted in the one or two position (i.e. symmetrical or asymmetrical) by saturated or unsaturated, branched or unbranched alkyl, such as dodecyl glycerol ether, decyl glycerol ether, octyl glycerol ether, propyl glycerol ether, octadecyl glycerol ether (batyl alcohol), hexadecyl glycerol ether (chimyl alcohol) and octadecenyl glycerol ether (selachyl alcohol). Preference is given to using 1-monoalkyl glycerol ether. Preference is given to 1-monoalkyl glycerol ethers with saturated (branched or unbranched) $C_3$- to $C_{18}$-hydrocarbon group, particularly preferably saturated and branched $C_6$- to $C_{12}$-hydrocarbon group. Very particular preference is given to 1-(2-ethylhexyl) glycerol ether (Sensiva® SC 50).

Aromatic alcohols are chosen from (i) aryloxyalkanols (glycol monoaryl ethers), (ii) arylalkanols and (iii) oligoalkanol aryl ethers.

(i) aryloxyalkanols used according to the invention have the formula Ar—O—$(CHR)_n$—OH, where R=independently H (when n≥2) or $C_1$- to $C_6$-alkyl, where n is an integer and preferably 2 to 10, more preferably 2 to 6 and in particular 2 or 3. While the group Ar may be a ring-substituted or unsubstituted aryl group, unsubstituted aryl, e.g. phenyl or naphthyl, are preferred. Examples of aryloxyalkanols used according to the invention are phenoxyethanol and phenoxypropanols. Preferred phenoxypropanols are 1-phenoxy-2-propanol, 2-phenoxy-1-propanol or mixtures thereof, and 3-phenoxy-1-propanol.

(ii) Arylalkanols used according to the invention have the formula Ar—$(CHR)_n$—OH, where R=independently H or $C_1$- to $C_6$-alkyl, where n is an integer and preferably 1 to 10, more preferably 1 to 6 and in particular 1, 2, 3 or 4. While the group Ar may be a ring-substituted or unsubstituted aryl group, unsubstituted aryl, e.g. phenyl or naphthyl, are preferred. Examples of arylalkanols are 3-phenyl-1-propanol, phenethyl alcohol, veratryl alcohol (3,4-dimethoxyphenylmethyl alcohol), benzyl alcohol and 2-methyl-1-phenyl-2-propanol. The (iii) oligoalkanol aryl ethers include, for example, phenoxy-di-, -tri- and -oligoethanol and phenoxydi-, -tri- and -oligopropanol.

In this connection, preference is given to an embodiment in which the component (b) comprises a mixture of phenoxyethanol and benzyl alcohol, where the component (b) more preferably consists of the mixture of phenoxyethanol and benzyl alcohol.

Further preferred mixtures comprise (A) phenethyl alcohol and phenoxyethanol, (B) majantol (2,2,-dimethyl-3-(3-methylphenyl)propanol) and phenoxyethanol, (C) 3-phenylpropanol and phenoxyethanol, (D) benzyl alcohol and majantol and phenoxyethanol or (E) benzyl alcohol and phenoxyethanol and phenoxypropanols.

In preferred stabilizer compositions according to the invention, the weight ratio of the aromatic alcohols b1:b2 is in the range from 1:100 to 100:1, such as in the range from 1:50 to 50:1, in the range from 1:20 to 20:1, in the range from 1:10 to 10:1, in the range from 1:5 to 5:1, in the range from 1:3 to 3:1, in the range from 1:2 to 2:1, in the range from 1:1.5 to 1.5:1 or in the range from 1:1.2 to 1.2:1. In particular, the weight ratio is about 1:1.

In a preferred stabilizer composition, (a) the glycerol monoalkyl ether is 1-(2-ethylhexyl) glycerol ether and (b) the mixture of at least two different aromatic alcohols is a mixture consisting of phenoxyethanol and benzyl alcohol, where the weight ratio of phenoxyethanol to benzyl alcohol is preferably about 1:1.

In a further embodiment according to the invention, the stabilizer composition is in the form of a working mixture (e.g. an aqueous working solution) and comprises a comparatively small amount of components (a) and (b), e.g. (a) 0.05 to 1% by weight, preferably 0.1 to 0.5% by weight, such as, for example, 0.2% by weight of one or more glycerol monoalkyl ethers, e.g. 1-(2-ethylhexyl) glycerol ether, and (b) 0.2 to 5% by weight, preferably 0.5 to 3% by weight, more preferably 1.5 to 2% by weight, of the mixture of at least two aromatic alcohols, preferably of the mixture of phenoxyethanol and benzyl alcohol. An example of a working mixture is a working solution. A preferred working solution is in the form of an aqueous solution and comprises more than 90% by weight of water, e.g. 95 to 99% by weight, more preferably 96 to 98.5% by weight, in particular about 98% by weight, of water. Particular preference is given to a working solution which comprises (a) 0.1 to 0.3% by weight of 1-(2-ethylhexyl) glycerol ether and (b) 1.5 to 2.0% by weight of phenoxyethanol. Alternatively, the working mixture may be in solid, paste, or high-viscosity form.

In a further embodiment of the invention, the stabilizer composition is in the form of concentrate and comprises comparatively large amounts of components (a) and (b). For example, a stabilizer composition in the form of a concentrate comprises (a) 1 to 30% by weight, preferably 2 to 20% by weight, more preferably 5 to 15% by weight, in particular about 10% by weight, of glycerol monoalkyl ether, preferably 1-(2-ethylhexyl) glycerol ether, and (b) 99 to 70% by weight, preferably 98 to 80% by weight, more preferably 95 to 85% by weight, in particular about 90% by weight, of the mixture of at least two different aromatic alcohols.

As well as comprising the components (a) and (b) according to the invention, the stabilizer composition according to the invention can comprise further components. However, it preferably has a low surfactant content and comprises less than 5% by weight of surfactant, preferably less than 2% by weight, particularly preferably less than 0.5% by weight, of surfactant and is particularly preferably surfactant-free. The further components may be solid, liquid or gaseous further active ingredients, functional additives or auxiliaries.

Preferred active ingredients, functional additives or auxiliaries are alcohols (e.g. lower alcohols, such as ethanol, propanols, glycols, such as 1,2-propylene glycol, glycol ether, diols, such as pentane-1,2-diol, polyols, such as glycerol) and other solvents, such as water, and emulsifiers, complexing agents, humectants, UV filters, skincare additives, antioxidants, thickeners, dyes, fragrances, electrolytes, pH regulators, pigments, stabilizers, polymers, medicaments and antimicrobial active ingredients (e.g. phenol derivatives, parabens, triclosan, iodopropinyl butylcarbamate (IPBC), dibromodicyanobutane (DBDCB), 2-bromo-2-nitro-1,3-propanediol (Bronopol), isothiazolones, quaternary ammonium compounds, biguanides, bispyridinium salts and formaldehyde donor compounds). The amount of antioxidants such as vitamin E α-tocopherol), BHA (tert-butyl-4-methoxyphenol) or BHT (2,6-di-tert-butyl-p-cresol) in the concentrate according to the invention may be up to 10% by weight, preferably up to 1% by weight and more preferably up to 0.1% by weight. The amounts of the preferred active ingredients, functional additives or auxiliaries, in particular the said antioxidants, in the working mixtures according to the invention vary within the scope of the amounts customary in cosmetic, pharmaceutical or technical products. With regard to the oxidation stabilization of glycerol monoalkyl ether-containing compositions, reference is made to DE-A-100 28 638.

Compositions according to the invention are preferably free from the dehydracetic acid proposed in DE-A-40 26 756, which is a yellow solid which is undesired in certain applications (e.g. in moist cloths) due to discoloration. In addition, the effect of dehydracetic acid and benzoic acid is limited to pH values of less than 6 and use of the said acid may result in corrosion, for which reason no organic acid chosen from the group of benzoic acid, 4-hydroxybenzoic acid, salicylic acid, formic acid, acetic acid, propionic acid, sorbic acid, undecylenic acid and dehydracetic acid or mixtures thereof, including their sodium, potassium, calcium, magnesium, ammonium and ethanolamine salts, is particularly preferably present.

In addition, preference is given to an embodiment in which the composition is free from polyhexamethylenebiguanide salt, which is a polymeric solid which has a tendency towardss precipitations at low temperatures and is incompatible with anionic surfactants. In addition, polyhexamethylenebiguanides are more strongly foaming than the compositions according to the invention and form a water-insoluble polymeric base in the alkaline medium.

Compositions according to the invention are preferably free from fragrances, such as phenethyl alcohol or majantol, and also phenoxybutanol or 3-n-octyloxypropan-1,2-diol. In a further embodiment, the presence of the mono- and oligoglycerol monocarboxylic monoesters proposed in DE-A-100 25 123, which hydrolyse under alkaline conditions, is excluded.

In one embodiment, the weight ratio x of component (a) to component (b) in the stabilizer composition according to the invention is 0.15 or less, preferably 0.13 or less, more preferably 0.12 to 0.05 and in particular about 0.11.

In addition, the invention relates to the use of a stabilizer composition for stabilizing (preserving) cosmetic, dermatological, pharmaceutical, technical and/or household products.

Due to the particular physiological compatibility, stabilizer compositions according to the invention have a broad field of use. They may be in the form of clear, homogeneous, e.g. aqueous, preparations, or in the form of low-viscosity or high-viscosity preparations, e.g. gels. The compositions are effective over a broad pH range and can be used in strongly acidic to strongly alkaline medium, preferably in the pH range from 3 to 11, particularly preferably 5 to 9.

Examples of preparations referred to here as product are:
1) technical products, such as biocide dispersions, dispersions in the agricultural sector, pesticide preparations, polymer dispersions, adhesives, thickeners, paints, coatings, pigment dispersions, photographic materials (e.g. developer solutions),
2) dermatological and cosmetic products, e.g. for topical application or as leave-on or rinse-off products, such as sunscreen preparations, moist cloths, polymeric preparations with film-forming properties, toothpastes, care products, make-up, lipsticks, nail varnish,
3) pharmaceutical preparations, such as isotonic solutions, medicaments and vaccines, and
4) disinfecting preparations, such as deodorants, foot deodorants, alcoholic spray disinfectants and compositions for manual instrument preparation.

Surfaces with which products stabilized according to the invention can be treated are
i) biological materials, such as skin, mucosa, wounds, plants, parts of plants,
ii) materials which come into contact with skin, mucosa or wounds, such as contact lenses or wound coverings,
iii) surfaces such as medicinal devices, medicinal instruments (e.g. endoscopes) or surfaces such as floors and operating tables.

The present invention offers, inter alia, the following advantages:
  The compositions can be formulated from inexpensive components.
  The compositions are pH neutral, not very aggressive (low corrosion) and correspondingly readily material-compatible.
  The stabilizer compositions are low-odour, low-emission, inert and readily compatible with other additives or auxiliaries, are toxicologically and ecotoxicologically safe, physiologically safe (good skin compatibility), readily storage-stable and can be washed off easily.
  The compositions have no discoloration tendency, are effective at short contact times and, due to the synergistic increase in effect, require a low active ingredient concentration.
  The compositions are low-foam and oxidation- and pH-stable.

Added to this is the fact that, surprisingly, according to the invention the desired high use concentrations can be achieved which are physically not possible with noninventive combinations of a) glycerol ether and b) aromatic alcohol (due to limited solubility of the substances in water), or are not permissible (due to prescribed maximum amounts of glycerol ether and aromatic alcohol). In addition, the use of the mixture of at least two aromatic alcohols which belong to different groups, enables relatively large amounts of the mild glycerol monoalyll ethers to be brought into aqueous solution. The thereby improved solubility and increased effectiveness of the combination due to the glycerol monoalkyl ether in some instances in turn allows the total amount of component b) chosen to be lower. Alternately, the at least two aromatic alcohols which belong to different groups also have a synergistic effect, and the final concentration of the combination according to the invention (composition) chosen can, despite the required high effectiveness, be comparatively low.

The compositions according to the invention thus solve the abovementioned problems in the prior art and have
- improved effectiveness (e.g. on the basis of a synergistic increase in effect),
- good stability due to a small decrease in active ingredient upon storage,
- insensitivity towards low and high pH values, towards low and high temperatures (they have low-temperature stability and are thermostable), and towards oxidizing and reducing agents,
- good compatibility with (cosmetic) ingredients, they thus represent a good alternative to other "soft" preservatives, such as parabens,
- multifunctional effect (e.g. as solvent, solubility promoter, stabilizer),
- due to the presence of the aromatic alcohols, also a vapour phase effect,
- worldwide-accepted ingredients of natural or near-natural origin, and
- good wettability of surfaces without foaming.

The compositions facilitate the incorporation of glycerol monoalkyl ethers into cosmetic formulations and act not only as antimicrobial stabilizers, they also have specific effects against selected microbial species, e.g. odour-causing microbes (deodorants), microbes which cause dandruff (anti-dandruff compositions), microbes which cause "skin impurities" (anti-acne compositions, compositions for treating blemished skin).

Preferred compositions according to the invention are also liquid at low temperatures and can thus be handled and metered easily.

Surprisingly, the odour of stabilizer compositions or stabilized products (e.g. also the odour of the aldehydes released as a function of time from aromatic alcohols, e.g. arylalkanols) is stabilized by the presence of the glycerol monoalkyl ether and antioxidant (virtually no increase in the aldehyde content over time). In this respect, the invention also relates to (oxidation- and/or colour- and/or odour) stabilized compositions which comprise (a) one or more 1- or 2-($C_1$- to $C_{24}$-alkyl) glycerol ethers (in particular 1-(2-ethylhexyl) glycerol ether), (b) one or more aromatic alcohols chosen from the groups of i) aryloxyalkanols, ii) arylalkanols and iii) oligoalkanol aryl ethers (preferably arylalkanol, in particular benzylalcohol) and (c) one or more antioxidants. Preference is given to using the antioxidants disclosed in DE 100 28 638. In particular, the addition of tocopherol and its derivatives (such as vitamin E) as antioxidant inhibits the destabilization of compositions comprising glycerol monoalkyl ether (such as 1-(2-ethylhexyl) glycerol ether) and aromatic alcohol (such as arylalkanol, e.g. benzyl alcohol) to form, for example, aromatic aldehyde (such as benzaldehyde). In this embodiment too, (b) a mixture of at least two different aromatic alcohols (b1, b2) chosen from the groups of i) aryloxyalkanols, ii) arylalkanols and iii) oligoalkanol aryl ethers is present in which the two different aromatic alcohols belong to different groups i), ii) and iii), as listed above in detail.

The advantages of the invention are evident in particular from the following examples.

EXAMPLES

Unless expressly stated otherwise, all of the percentages are percentages by weight. Aqueous working solutions were investigated using Ringer's solution as product in the Koko test.

The following abbreviations are used:
SC 50 1-(2-ethylhexyl) glycerol ether, Sensiva® 50
Water demineralized water
POE phenoxyethanol
BA benzyl alcohol Investigation Principle Using the described method, the effectiveness of chemical preservatives (stabilizer compositions) is tested with regard to the pack preservation for cosmetic formulations. For this purpose, the compositions to be investigated are added in varying concentrations to the unstabilized samples in various experimental batches. A continuous microbial burden is achieved by periodically inoculating the experimental batches. In parallel to the inoculation, streaks of each of the individual batches are in each case made immediately beforehand. Assessment is made by reference to the microbial growth of the streaks. The longer the period before the first appearance of microbial growth, the more effective the composition.

Solutions and Nutrient Media
CSA (casein peptone soya flour peptone agar)
SA (Sabouraud dextrose agar)
SA slant tube
CSA+TLSH (No. 4)
SA-TLSH (No. 10)
NaCl (physiological sodium chloride solution, 8.5%)
TLSH (disinhibiting medium for bacteria=Tween 80+lecithin+saponin+histidine)

The test microbe used was the mixed suspension (Group 5) of the following four test microbe groups.

| | | |
|---|---|---|
| Group 1 | *Staphylococcus aureus* | ATCC 6538 |
| (Koko 1) | *Staphylococcus epidermis* | ATCC 12228 |
| Group 2 | *Enterobacter gergoviae* | Dr Eigener/ |
| (Koko 2) | | Beiersdorf 1994 |
| | *Escherichia coli* | ATCC 11229 |
| | *Klebsiella pneumoniae* | ATCC 4352 |
| Group 3 | *Pseudomonas aeruginosa* | ATTC 15442 |
| (Koko 3) | *Pseudomonas fluorescens* | ATCC 17397 |
| | *Pseudomonas putida* | ATCC 12633 |
| Group 4 | *Aspergillus niger* | ATCC 6275 |
| (Koko 4) | *Penicillium funiculosum* | ATCC 36839 |
| | *Candida albicans* | ATCC 10231 |

Cultivation of the Test Microbes
Bacteria: streaking using a sterile glass rod on CS agar
Yeasts: streaking using a sterile glass rod on SA agar
Fungi: *Aspergillus niger* is transferred to 4 SA slant tubes
*Penicillium funiculosum* is transferred to SA agar plates
All of the test microbes are incubated for one week at 25° C.±2° C. The test microbes are replaced at intervals of 3 to 4 months.

Preparation of the Inoculation Solution (Groups 1 to 3)
The bacteria are rinsed off with 5 ml of NaCl solution in each case, filtered through a glass funnel containing glass wool into a 100 ml measuring cylinder and made up to 100 ml with NaCl. The bacterial suspensions have a titre of about $10^9$ CFU/ml.

Preparation of the Inoculation Solution (Group 4)

Three *Aspergillus niger* slant tubes are each shaken with 3 ml of NaCl solution on a Heldolph stirrer and introduced through a glass funnel containing glass wool. The yeast *Candida albicans* is rinsed off with 5 ml of NaCl and likewise poured through the glass funnel. 5 ml of a *Penicillium funiculosum* suspension are added to this mixture and made up to 100 ml with NaCl. The fungal suspension has a titre of about $10^{5-9}$ CFU/ml.

Preparation of the Inoculation Solution (Group 5)

The inoculation solution actually used is prepared as described above (Groups 1 to 4). After rinsing off, these are mixed and then made up to 100 ml with NaCl.

The microbial suspension was transferred to sterile glass-stoppered bottles containing glass beads and shaken for 5 min at a shaking frequency (to-and-fro movement) of 200 units/min. The microbial content of the mixed suspension is $10^9$ CFU/ml. The suspension should be used on the day of preparation, but can also be used after 24 hours upon storage in a refrigerator.

Implementation

In separate batches, 25 g of the cosmetic to be tested are mixed in each case with the compositions to be investigated in varying concentrations. The growth control used in each case is an unstabilized product sample. The test batches are streaked onto CSA/TLSH and SA/TLSH once per week following thorough stirring using a sterile glass rod, the first streaking being carried out directly prior to reinoculation. All of the samples are inoculated with 0.1 ml of the respective microbial suspension and thoroughly stirred.

The microbial growth of the streaks is assessed after incubation for three days at 25° C.±2° C. To be on the safe side, negative streaks are observed for a further two days and reassessed. The stabilizing action of the individual product concentration is assessed in a semiqualitative method by means of the growth of the individual streaks.

The test is usually carried out over six inoculation cycles and terminated after massive growth on two occasions.

Assessment of the Results

A composition is considered good if it exists under the laboratory conditions given above for a period of six weeks without microbial attack of the sample batches, i.e. even after the sixth inoculation, no microbial growth can be detected.

The effectiveness of various preservatives was tested:
1) Suttocide A (50% strength)=sodium hydroxymethyl-glycinate (comparison)
2) Glydant XL 1000=dimethyldimethylolhydantoin (comparison)
3) Concentrate according to the invention (10% by weight of SC 50, 45% by weight of BA and 45% by weight of POE)
4) Concentrate comprising 50% by weight of BA and 50% by weight of POE (comparison)

| Koko results: | | Inoculation cycles | | | | | |
|---|---|---|---|---|---|---|---|
| | | 1 | 2 | 3 | 4 | 5 | 6 |
| 1) | 0.5% | +Y | +Y | +Y | +Y | +Y | +Y |
| 2) | 0.6% | +B | ++B | ++B | ++B | ++B | ++B |
| 3) | 2.0% | − | − | − | − | − | − |
| 4) | 2.0% | +Y | +++BY | +Y | +Y | +++BY | +++YB |

Y = yeast growth
B = bacterial growth
No growth (−) or growth weak (+) to considerable (+++).

Result:

Significant increase in the activity of the combination of benzyl alcohol and phenoxyethanol in the presence of 10% by weight of Sensiva SC 50, based on the concentrate.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method which may be used for stabilizing cosmetic products with a composition, said method comprising:
    combining said composition with said cosmetic products, wherein said composition comprises:
    a) from 5% to 15% by weight 1-(2-ethylhexyl) glycerol ether;
    b) from 95% to 85% by weight of a mixture selected from the group consisting of:
    b1) phenoxy ethanol and b2) benzyl alcohol, and
    b1) phenoxy propanol and b2) benzyl alcohol; and
    c) vitamin E,
    wherein a) and b) are present in a weight ratio a)/b) of less than 0.15, and
    wherein b1 and b2 are present in a weight ratio b1/b2 of between 1/2 and 2/1.

2. The method of claim 1, wherein said composition comprises: a) about 10%, by weight, of 1-(2-ethylhexyl) glycerol ether; and b) about 90%, said mixture of phenoxy ethanol and benzyl alcohol.

3. The method of claim 1, wherein said ratio is less than about 0.13.

4. The method of claim 3, wherein said ratio is between about 0.05 and about 0.12.

5. The method of claim 4, wherein said ratio is about 0.11.

* * * * *